United States Patent [19]

Tessier et al.

[11] Patent Number: 4,757,127

[45] Date of Patent: Jul. 12, 1988

[54] PREPARATION OF FLUORINE DERIVATIVES OF PHOSPHONIC ACID

[75] Inventors: Jean Tessier, Vincennes; Van T. Truong, Montfermeil, both of France

[73] Assignee: Roussel Uclaf, Paris, France

[21] Appl. No.: 933,031

[22] Filed: Nov. 20, 1986

[30] Foreign Application Priority Data

Nov. 20, 1985 [FR] France .................. 85 17145

[51] Int. Cl.$^4$ .............................................. C07F 9/40
[52] U.S. Cl. .................................... 558/141; 558/303; 560/231
[58] Field of Search ............... 558/141, 303; 560/231

[56] References Cited

PUBLICATIONS

Umemoto et al., "Tetrahedron Letters," vol. 27, No. 28, (1986) pp. 3271–3274.
Reactions Chemiques Dangereuses, (1974) pp. 421–427.
Blackburn et al., "Chem. Abs.," vol. 103, (1985) 71409w.
Fokin et al., "Chem. Abs.," vol. 74, (1971) 124736s.
Grell et al., "Chem. Abs.," vol. 65, (1966) 7210h.
Grieco et al., "J. Med. Chem.", vol. 23, (1983) pp. 1077–1083.

Primary Examiner—Anton H. Sutto
Attorney, Agent, or Firm—Bierman and Muserlian

[57] ABSTRACT

A process for the preparation of phosphonic acid compounds of the formula

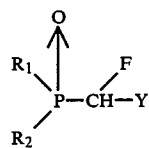

wherein $R_1$ and $R_2$ are individually selected from the group consisting of aryl of 6 to 14 carbon atoms, optionally unsaturated alkyl of 1 to 8 carbon atoms, aryloxy of 6 to 14 carbon atoms, optionally unsaturated alkoxy of 1 to 8 carbon atoms and aralkoxy and aralkyl of 7 to 18 carbon atoms, or $R_1$ and $R_2$ together with a phosphorus atom form a ring, Y is selected from the group consisting of

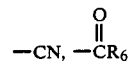

and —COOR$_3$, R$_3$ is selected from the group consisting of optionally unsaturated alkyl of 1 to 8 carbon atoms and optionally substituted, and

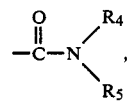

$R_4$ and $R_5$ are individually selected from the group consisting of hydrogen, optionally unsaturated alkyl of 1 to 8 carbon atoms and aryl of 6 to 14 carbon atoms and $R_6$ is selected from the group consisting of optionally unsaturated alkyl of 1 to 10 carbon atoms, optionally unsaturated cycloalkyl of 3 to 10 carbon atoms and aryl of 6 to 14 carbon atoms comprising reacting a compound of the formula

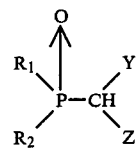

wherein $R_1$, $R_2$ and Y have the above definitions and Z is selected from the group consisting of —CHO and

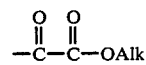

and Alk is optionally unsaturated alkyl of 1 to 8 carbon atoms with fluorine to obtain the corresponding compound of formula I.

9 Claims, No Drawings

PREPARATION OF FLUORINE DERIVATIVES OF PHOSPHONIC ACID

STATE OF THE ART

Grell et al [Liebigs Ann. Chem., Vol. 693 (1965), p. 141] describes the preparation of ethyl(O,O-diethyl-phosphono)-2-fluoro-2-acetate by reacting perchloryl fluoride, potassium enolate of diethylphosphono diethyl oxalacetate at −10° C. in absolute alcohol by the following reaction

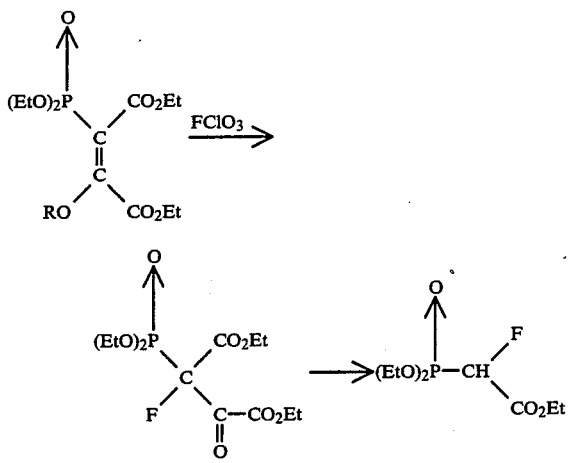

While perchloryl fluoride is a useful reagent for adding fluorine to compounds having a mobile hydrogen, it can not be used on an industrial scale because of the risk of violent explosions.

Other pertinent prior art are Chem. Abs., Vol. 74 (1971), p. 402, No. 124736s and Vol. 103 (1985), p. 661, No. 71409w and J. Med. Chem., Vol. 23, No. 10 (1980), p. 1077-1083.

OBJECTS OF THE INVENTION

It is an object of the invention to provide a novel process of the compounds of formula I free of the defects of the prior art.

It is another object of the invention to provide the novel compounds of formula I with the proviso that if $R_1$ and $R_2$ are ethoxy, Y is not $-COOCH_2CH_3$.

These and other objects and advantages of the invention will become obvious from the following detailed description.

THE INVENTION

The novel process of the invention for the preparation of phosphonic acid compounds of the formula

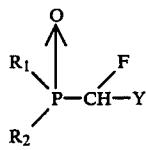   I wherein $R_1$ and $R_2$ are individually selected from the group consisting of aryl of 6 to 14 carbon atoms, optionally unsaturated alkyl of 1 to 8 carbon atoms, aryloxy of 6 to 14 carbon atoms, optionally unsaturated alkoxy of 1 to 8 carbon atoms and aralkoxy and aralkyl of 7 to 18 carbon atoms, or $R_1$ and $R_2$ together with a phosphorus atom form a ring, Y is selected from the group consisting of

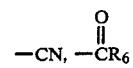

and $-COOR_3$, $R_3$ is selected from the group consisting of optionally unsaturated alkyl of 1 to 8 carbon atoms and optionally substituted, and

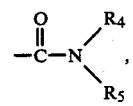

$R_4$ and $R_5$ are individually selected from the group consisting of hydrogen, optionally unsaturated alkyl of 1 to 8 carbon atoms and aryl of 6 to 14 carbon atoms and $R_6$ is selected from the group consisting of optionally unsaturated alkyl of 1 to 10 carbon atoms, optionally unsaturated cycloalkyl of 3 to 10 carbon atoms and aryl of 6 to 14 carbon atoms comprises reacting a compound of the formula

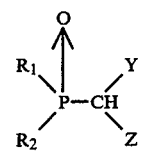   II wherein $R_1$, $R_2$ and Y have the above definitions and Z is selected from the group consisting of $-CHO$ and

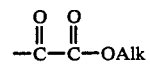

and Alk is optionally unsaturated alkyl of 1 to 8 carbon atoms with fluorine to obtain the corresponding compound of formula I.

The process has the advantage that it can be used on an industrial scale without the danger of explosions and gives good yields. In view of the extreme reactivity of fluorine, it was surprising that the process yielded the monofluoride derivatives of formula I and not the difluorides of the formula

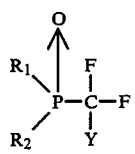

and fluorine could also have been expected to cause secondary reactions at $R_1$ and $R_2$.

Examples of $R_1$ and $R_2$ are aryl such as phenyl; alkyl such as methyl, ethyl, n-propyl, isopropyl, n-butyl, sec.-butyl, isobutyl, n-pentyl, n-hexyl and tert.-butyl; aralkyl such as benzyl and phenethyl; aryloxy such as phenoxy; alkoxy such as methoxy, ethoxy, n-propoxy, isopropoxy, n-butoxy, sec.-butoxy, isobutoxy and tert.-butoxy; and aralkoxy such as benzoxy and phenethoxy.

When rings are formed by $R_1$ and $R_2$ and the phosphores atom, $R_1$ and $R_2$ are 1,2-dimethyl-ethylenedioxy, 1,1,2,2-tetramethylethylenedioxy, propylene-1,3-dioxy or 2,2-dimethylpropylene-1,3-dioxy.

Examples of $R_3$ and Alk are methyl, ethyl, n-propyl, isopropyl, n-butyl, sec.-butyl, isobutyl, tert.-butyl and n-pentyl. When $R_4$ and $R_5$ are alkyl, they are preferably methyl, ethyl, n-propyl, isopropyl or n-butyl and when they are aryl, they are preferably phenyl.

Examples of $R_6$ are alkyl such as methyl, ethyl, n-propyl, isopropyl, n-butyl, sec.-butyl, tert.-butyl, n-pentyl and n-hexyl; cycloalkyl such as cyclopropyl, cyclobutyl, cyclopentyl and cyclohexyl; and aryl such as phenyl.

Preferably, the reaction of the compound of formula II and fluorine is effected in the presence of a basic agent such as alkali metal and alkaline earth metal carbonates, bicarbonates and hydroxides such as sodium hydroxide or potassium hydroxide. Preferably, a current of fluorine containing 5 to 20% by volume of an inert gas such as nitrogen is used for the fluorinations.

The compounds of formula I are useful as intermediates for the preparation of pesticides, for combatting insects or acaricides and animal and vegetable parasites and are useful with the Wittig reaction to produce a very large number of biologically active products.

The compounds of formula I are useful for the production of pesticides as described in European Pat. No. 0,050,534 wherein a cis aldehyde in the form of a lactone of the formula

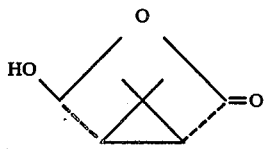
V is reacted in the presence of a strong base by the Wittig reaction with a phosphonate of the formula

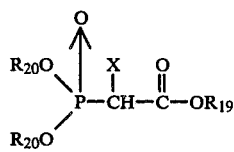
VI wherein X is halogen and $R_{19}$ and $R_{20}$ are alkyl to form a compound of the formula

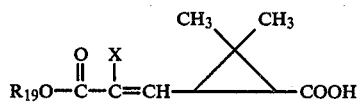

which is then reacted with an alcohol of the formula B—OH wherein B is the residue of an alcohol used in pyrethrinoid esters.

The compounds of formula II are generally known and those wherein Z is —CHO may be prepared as follows:

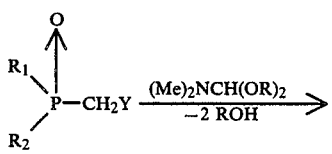

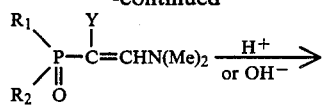

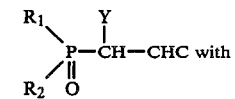

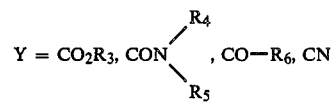

$Y = CO_2R_3, CON\begin{smallmatrix}R_4\\R_5\end{smallmatrix}, CO-R_6, CN$

Other compounds of formula II are described by Yoffe et al [Tetrahedron, Vol. 28 (1972), p. 2783–2798] and the compound of formula II wherein $R_1$ and $R_2$ are —OCH$_2$CH$_3$ and Y is COOCH$_2$CH$_3$ and Z is

is described in the examples.

In a preferred mode of the process, a compound of formula II wherein Z is —CHO or its salified form is reacted in acetonitrile and a slightly basic aqueous medium with fluorine.

In a preferred mode of the process, a compound of the formula

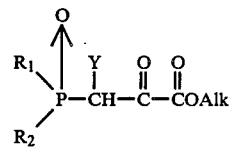
II$_A$' or its salified form

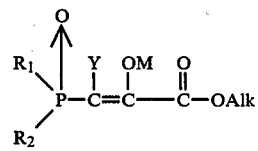
II$_B$' wherein M is an alkali metal or alkaline earth metal and $R_1$, $R_2$, Y and Alk have the above definitions are reacted with fluorine in a compatible organic solvent and the resulting product is treated with a basic aqueous solution to obtain the compound of formula I. The alkali metal is preferably sodium or potassium.

In a preferred mode of the invention, the compounds of formula II$_A$' or II$_B$' are reacted with fluorine in a basic aqueous medium.

In a preferred mode of the process of the invention, $R_1$ and $R_2$ are linear alkoxy of 1 to 4 carbon atoms, Y is —COOR$_3$ and R$_3$ is optionally unsaturated alkyl of 1 to 6 carbon atoms, Y is

or —CN and $R_6$ is aryl of 6 to 14 carbon atoms or optionally unsaturated alkyl of 1 to 6 carbon atoms.

In the following examples there are described several preferred embodiments to illustrate the invention. However, it is to be understood that the invention is not intended to be limited to the specific embodiments.

EXAMPLE 1

Ethyl(O,O-diethyl-phosphono)-2-fluoro-2-acetate

STEP A: Potassium salt of 3-(O,O-diethyl-phosphono)-1,4-diethoxy-1,4-dioxo-2-buten-2-ol 25.3 ml of ethanol were added to 6.7 g of potassium in 100 ml of ethyl ether, and the mixture was refluxed for 4 hours. A mixture of 25 g of ethyl oxalate and 38.4 g of ethyl(O,O-diethyl-phosphono)acetate was introduced over about 10 minutes and the resulting mixture was refluxed for a further 2 hours. The mixture was stirred for 20 hours at 20° C. and the precipitate formed was separated, washed with ethyl ether to obtain 23.4 g of potassium salt of 3-(O,O-diethyl-phosphono)-1,4-diethoxy-1,4-dioxo-2-buten-2-ol melting at 160° C.

STEP B: Ethyl(O,O-diethyl-phosphono)-2-fluoro-2-acetate

A current of fluorine diluted to 10% in nitrogen was passed through a solution of 1.45 g of potassium salt of 3-(O,O-diethyl-phosphono)-1,4-diethoxy-1,4-dioxo-2-buten-2-ol in 15 ml of chloroform and 10 ml of trichlorofluoromethane cooled to −60° C. After standing for one hour at −60° C., the mixture was heated to 0° C. under nitrogen to expel excess fluorine and then a solution of sodium bicarbonate and sodium thiosulfate was added. The mixture was stirred and the decanted aqueous base was extracted with methylene chloride. The organic phase was concentrated to dryness by distillation and the residue was purified by chromatography over silica. Elution with a mixture of hexane and ethyl acetate (1-1) yielded 0.65 g of ethyl(O,O-diethyl-phosphono)-2-fluoro-2-acetate, pure in T.L.C. with a Rf=0.2.

EXAMPLE 2

Ethyl(O,O-diethyl-phosphono)-2-fluoro-2-acetate 1.45 g of potassium salt of 3-(O,O-diethyl-phosphono)-1,4-diethoxy-1,4-dioxo-2-buten-2-ol and 1.2 g of potassium bicarbonate were dissolved in 20 ml of water cooled to 0°/+2° C. and a current of fluorine diluted to 10% in nitrogen was bubbled in until the necessary quantity of fluorine was absorbed. A sweeping with nitrogen was carried out for 1 hour at 0° C. to expel excess fluorine and then sodium thiosulfate was added. After extraction with methylene chloride and concentration to dryness by distillation, 0.94 g of ethyl(O,O-diethyl-phosphono)-2-fluoro-2-acetate were obtained.

EXAMPLE 3

Ethyl(O,O-diethyl-phosphono)-2-fluoro-2-acetate 36 g of ethyl 2-(O,O-diethyl-phosphono)-3-hydroxy-2-propenoate [prepared by the process described by DAWSON et al., J.A.C.S. Vol 74, p. 5312 (1952)] were dissolved in 720 ml of water containing 43 g of sodium bicarbonate and cooled to +3° C. A current of 10% fluorine in nitrogen was passed through for 6 hours and then excess fluorine was expelled by a current of nitrogen. Any possible remaining excess fluorine was reduced by addition of sodium thiosulfate. Extraction was effected with methylene chloride and the extracts were concentrated to dryness by distillation under reduced pressure to obtain 25.6 g of crude product. 23 g of the crude product were distilled under reduced pressure to obtain 16.5 g of ethyl(O,O-diethyl-phosphono)-2-fluoro-2-acetate with a boiling point of 110° C. at 0.8 mm of mercury.

EXAMPLE 4

Dimethyl ester of (1-fluoro-2-oxo-propyl)-phosphonic acid

A mixture of 25 g of dimethyl[1-(hydroxymethylene)-2-oxo-propyl]phosphonate, 500 ml of water and 32.7 g of sodium bicarbonate was cooled to 0°/+2° C. with stirring under nitrogen and a current of 10% fluorine in nitrogen was bubbled in for 5 hours. The residual fluorine was expelled by a current of nitrogen and sodium thiosulfate was added. The mixture stood for 16 hours at about 0° C. and after extraction with chloroform, drying and distilling to dryness under reduced pressure, 15 g of product were obtained. The latter was chromatographed over silica and was eluted with hexane-ethyl acetate mixture (1-1) to obtain 9.47 g of dimethyl ester of (1-fluoro-2-oxo-propyl)phosphonic acid with Rf=0.27. (CHCl$_3$-acetone-hexane:1-1-1).

EXAMPLE 5

Diethyl ester of [3,3-dimethyl-1-fluoro-2-oxo-butyl]-phosphonic acid

A solution of 3.17 g of diethyl[3,3-dimethyl-1-(hydroxymethylene)-2-oxobutyl]phosphonate, 60 ml of water and 4 g of sodium bicarbonate was cooled to 0°/+5° C. under nitrogen and a current of fluorine diluted to 10% in nitrogen was bubbled for 1 hour in the solution under strong stirring. The current of fluorine was stopped and a current of nitrogen was passed through to expel residual fluorine. A small amount of sodium thiosulfate was added and the solution was extracted with methylene chloride. The extracts were dried, distilled under reduced pressure to obtain 2.68 g of product which was chromatographed over silica. Elution with hexane-ethyl acetate mixture (1-1) yielded 0.42 g of diethyl ester of [3,3-dimethyl-1-fluoro-2-oxo-butyl]phosphonic acid with a Rf=0.25.

EXAMPLE 6

Diethyl ester of (1-fluoro-2-oxo-phenyl ethyl)-phosphonic acid 6 g of potassium bicarbonate were added to a solution of 6.1 g of diethyl(1-benzoyl-2-hydroxyethenyl)-phosphonate, 120 ml of demineralized water and 60 ml of methyl cyanide and the solution was cooled to 0°/+2° C. under nitrogen. A current of 10% fluorine in nitrogen was bubbled in for about 1 hour and after the influx of fluorine was stopped, a current of nitrogen was passed through for 30 minutes. A small amount of sodium thiosulfate was added and the mixture was extracted with chloroform. The extracts were dried and distilled to dryness and the residue was chromatographed over silica. Elution with hexane-ethyl acetate mixture (1-1) yielded 3.64 g of diethyl ester of (1-fluoro-2-oxo-phenyl ethyl)-phosphonic acid with a Rf=0.50. (CHCl$_3$—acetone-hexane:1-1-1).

EXAMPLE 7

Diethyl ester of fluorocyanomethyl phosphonic acid

A solution of 40.5 g of sodium salt of 3-cyano-2-(O,O-diethyl-phosphono)-1-propen-1-ol [prepared by KIRILOV MONATSCH 99, 166 (1960)] and 800 ml of water was cooled in an ice bath under an atmosphere of nitrogen and with stirring to about 3° C. 44.9 g of sodium bicarbonate were added at 3° C. and a current of fluorine at 10% in nitrogen was bubbled in. After 6 hours and 50 minutes, the introduction of fluorine was stopped and a small amount of sodium thiosulfate was added to the reaction mixture which was then extracted with methylene chloride. The extracts were dried and distilled to dryness under reduced pressure to obtain 24.1 g of residue which was chromatographed over silica and eluted with hexane-ethyl acetate mixture (1-1) to obtain 21.0 g of diethyl ester of fluorocyanomethyl phosphonic acid with an Rf=0.3.

Various modifications of the products and process of the invention may be made without departing from the spirit or scope thereof and it should be understood that the invention is intended to be limited only as defined in the appended claims.

What we claim is:

1. A process for the preparation of phosphonic acid compounds of the formula

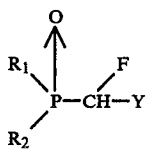

wherein $R_1$ and $R_2$ are individually selected from the group consisting of aryl of 6 to 14 carbon atoms, alkyl of 1 to 8 carbon atoms, alkenyl and alkynyl of 2 to 8 carbon atoms, aryloxy of 6 to 14 carbon atoms, alkoxy of 1 to 8 carbon atoms, alkenyloxy and alkynyloxy of 2 to 8 carbon atoms and aralkoxy and aralkyl of 7 to 18 carbon atoms, or $R_1$ and $R_2$ together with a phosphorus atom form a ring, Y is selected from the group consisting of

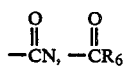

and —COOR$_3$, R$_3$ is selected from the group consisting of alkyl of 1 to 8 carbon atoms, alkenyl and alkynyl of 2 to 8 carbon atoms, and

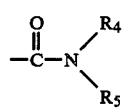

R$_4$ and R$_5$ are individually selected from the group consisting of hydrogen, alkyl of 1 to 8 carbon atoms, alkenyl and alkynyl of 2 to 8 carbon atoms and aryl of 6 to 14 carbon atoms and R$_6$ is selected from the group consisting of alkyl of 1 to 10 carbon atoms, alkenyl and alkynyl of 2 to 10 carbon atoms cycloalkyl and cycloalkenyl of 3 to 10 carbon atoms and aryl of 6 to 14 carbon atoms comprising reacting a compound of the formula

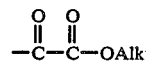

wherein $R_1$, $R_2$ and Y have the above definitions and Z is selected from the group consisting of —CHO and

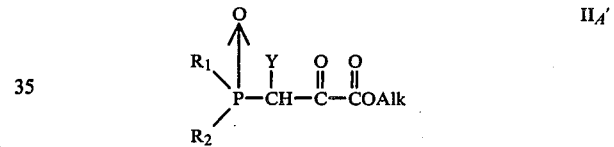

and Alk is alkyl of 1 to 8 carbon atoms or alkenyl or alkynyl of 2 to 8 carbon atoms with 5 to 20% by volume of fluorine in the presence of a basic agent to obtain the corresponding compound of formula I.

2. The process of claim 1 wherein Z is —CHO or its salified form and the reaction is effected in a slightly basic aqueous medium.

3. The process of claim 2 wherein acetonitrile is present.

4. The process of claim 1 wherein a compound of the formula

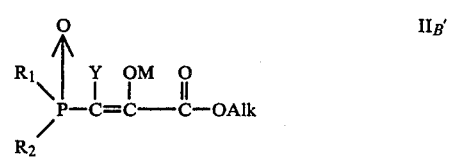

or its salified form

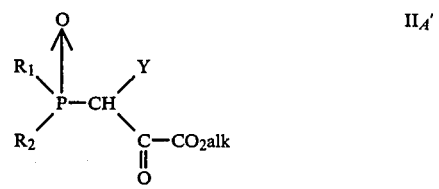

wherein M is an alkali metal or alkaline earth metal and $R_1$, $R_2$, Y and Alk have the above definitions are reacted with fluorine in a compatible organic solvent and the resulting product is treated with a basic aqueous solution to obtain the compound of formula I.

5. The process of claim 1 wherein a compound of the formula

II$_A'$ $$\begin{array}{c} O \\ R_1 \diagdown \Big\Uparrow \diagup Y \\ P-CH \\ R_2 \diagup \diagdown C-CO_2alk \\ \| \\ O \end{array}$$

or

-continued

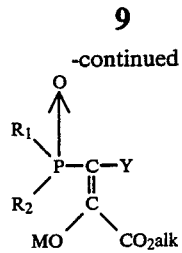
II$_{B'}$ wherein M is alkali metal or an alkaline earth metal and R$_1$, R$_2$, Y and Alk have the above definitions is reacted with fluorine in a basic aqueous solution to obtain a compound of formula I.

6. The process of claim 1 wherein R$_1$ and R$_2$ are linear alkyloxy of 1 to 4 carbon atoms.

7. The process of claim 1 wherein Y is —CN.

8. The process of claim 1 wherein Y is

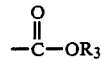

and R$_3$ is optionally unsaturated alkyl of 1 to 6 carbon atoms.

9. The process of claim 1 wherein Y is

and R$_6$ is aryl of 6 to 14 carbon atoms or alkyl of 1 to 6 carbon atoms.

* * * * *

UNITED STATES PATENT AND TRADEMARK OFFICE
CERTIFICATE OF CORRECTION

PATENT NO. : 4,757,127

DATED : July 12, 1988

INVENTOR(S) : JEAN TESSIER, JEAN-PIERRE DEMOUTE and VAN THUONG TRUONG

It is certified that error appears in the above-identified patent and that said Letters Patent is hereby corrected as shown below:

| Col. | Line | | |
|---|---|---|---|
| [75] | Title page: | Assignee Left Out | --JEAN-PIERRE DEMOUTE Montreuil, France-- |
| | | "T" should be | --Thuong-- |
| 3 | 18 | "5 to 20%" should be | --95 to 80%-- |
| 7 | claim 1 | "$-\overset{O}{\underset{}{C}}N,-\overset{O}{\underset{}{C}}R_6$" should be | --$-CN,-\overset{O}{\underset{}{C}}R_6$-- |

Signed and Sealed this

Thirteenth Day of December, 1988

Attest:

DONALD J. QUIGG

Attesting Officer   Commissioner of Patents and Trademarks